(12) United States Patent
Frostegård et al.

(10) Patent No.: US 9,682,122 B2
(45) Date of Patent: Jun. 20, 2017

(54) COMPOUNDS AND METHODS FOR THE TREATMENT OF VASCULAR DISEASE

(71) Applicant: ANNEXIN PHARMACEUTICALS AB, Veberöd (SE)

(72) Inventors: Johan Frostegård, Stockholm (SE); Knut Pettersson, Göteborg (SE)

(73) Assignee: ANNEXIN PHARMACEUTICALS AB, Stockholm (SE)

( * ) Notice: Subject to any disclaimer, the term of this patent is extended or adjusted under 35 U.S.C. 154(b) by 0 days.

(21) Appl. No.: 15/147,377

(22) Filed: May 5, 2016

(65) Prior Publication Data

US 2016/0235811 A1    Aug. 18, 2016

Related U.S. Application Data

(60) Continuation of application No. 14/447,782, filed on Jul. 31, 2014, which is a division of application No. 12/808,947, filed as application No. PCT/GB2008/004195 on Dec. 18, 2008, now Pat. No. 8,809,497.

(60) Provisional application No. 61/014,594, filed on Dec. 18, 2007.

(51) Int. Cl.
| | | |
|---|---|---|
| *C07K 14/47* | (2006.01) |
| *A61K 38/17* | (2006.01) |
| *A61K 31/4365* | (2006.01) |
| *A61K 31/616* | (2006.01) |
| *A61K 38/49* | (2006.01) |
| *A61K 47/48* | (2006.01) |
| *A61K 45/06* | (2006.01) |
| *A61K 9/00* | (2006.01) |

(52) U.S. Cl.
CPC ........ *A61K 38/1709* (2013.01); *A61K 9/0019* (2013.01); *A61K 31/4365* (2013.01); *A61K 31/616* (2013.01); *A61K 38/49* (2013.01); *A61K 45/06* (2013.01); *A61K 47/48215* (2013.01)

(58) Field of Classification Search
CPC ............................ C07K 14/47; A61K 38/1709
USPC .......................................... 530/350; 514/16.4
See application file for complete search history.

(56) References Cited

U.S. PATENT DOCUMENTS

| 7,635,676 B2 | 12/2009 | Allison |
| 7,645,739 B2 | 1/2010 | Allison |
| 2005/0164926 A1 | 7/2005 | Wun |
| 2005/0222030 A1 | 10/2005 | Allison |
| 2005/0222060 A1 | 10/2005 | Bot et al. |
| 2005/0267030 A1 | 12/2005 | Tsao et al. |
| 2005/0288372 A1 | 12/2005 | Ron |
| 2006/0009381 A1 | 1/2006 | Reutelingsperger |
| 2006/0105952 A1 | 5/2006 | Allison |
| 2006/0211020 A1 | 9/2006 | Farrer et al. |
| 2006/0258584 A1 | 11/2006 | Lind et al. |
| 2007/0015705 A1 | 1/2007 | Allison |

FOREIGN PATENT DOCUMENTS

| JP | 2005-523945 | 8/2005 |
| JP | 2006-117645 | 5/2006 |
| JP | 2007-521324 | 8/2007 |
| JP | 2007-532617 | 11/2007 |
| WO | WO 02/067854 | 9/2002 |
| WO | WO 2005/035001 | 4/2005 |
| WO | WO 2005/099744 | 10/2005 |
| WO | WO 2006/017578 | 2/2006 |
| WO | WO 2006/033287 | 3/2006 |
| WO | WO 2006/124161 | 11/2006 |
| WO | WO 2007/069895 | 6/2007 |
| WO | WO 2007/073509 | 6/2007 |

OTHER PUBLICATIONS

"tRNA", Concepts in Biochemistry—Structure Tutorials, retrieved from http://www.wiley.com/college/boyer/0470003790/structure/tRNA/trna_intro.htm on May 19, 2016.
Basaran et al., "Endothelial nitric oxide synthase gene intron 4 (VNTR) polymorphism and vascular access graft thrombosis", Journal of Investigative Surgery, 20:49-53, 2007.
Bhadra et al., "Pegnology: a review of PEG-ylated systems," Pharmazie, 57; 5-29, 2000.
Borroni et al., "Endothelial nitric oxide synthase (Glu298Asp) polymorphism is an independent risk factor for migraine with aura," Headache 46(10); 1575-1579, 2006.
Cederholm & Frostegard, "Annexin A5 as a novel player in prevention of atherothrombosis in SLE and in the general population," An.n N Y Acad Sci. 1108; 96-103, 2007.
Cederholm et al., "Decreased binding of annexin V to endothelial cells: a potential mechanism in atherothrombosis of patients with systemic lupus erythematosus," Arterioscler. Throbm. Vasc. Biol., 25(1):198-203, 2005.
Cederholm et al., "Mo-W10:3 Decreased annexin A5 in binding to endothelium is associated with cardiovascular disease in systemic lupus erythematosus and inhibited by IVIG," Atherosclerosis (Supplements), 7(3):29, 2006.
Chobanian, "Clinical practice. Isloated systolic hypertension in the elderly," N. Engl. J. Med., 357(8):789-796, 2007.
de Laat et al., "Annexin A5 polymorphism (-1C→T) and the presence of anti-annexin A5 antibodies in the antiphospholipid syndrome", Ann Rheum Dis., 65:1468-1472, 2006.

(Continued)

Primary Examiner — David Lukton
(74) Attorney, Agent, or Firm — Parker Highalnder PLLC

(57) ABSTRACT

The present invention relates to a method for the treatment of vascular dysfunction, reducing ischemic pain and/or treatment of a vascular disease comprising administering a therapeutically effective amount of Annexin A5 or a functional analog or variant thereof to a patient in need of such treatment. The vascular dysfunction, ischemic pain and/or vascular disease may be associated with impaired endothelium mediated vasodilatation, a reduced eNOS activity, and/or a reduced NO bioavailability. The patient may be suffering from a disease selected from angina pectoris, ischemic heart disease, peripheral artery disease, systolic hypertension, migraine, type 2 diabetes and erectile dysfunction.

3 Claims, 3 Drawing Sheets

(56) References Cited

OTHER PUBLICATIONS

Doshi et al., "Flow-mediated dilatation following wrist and upper arm occlusion in humans: the contribution of nitric oxide," *Clin. Sci. (Lond.)*, 101(6):629-935, 2001.

Duplain et al., "Insulin resistance, hyperlipidemia, and hypertension in mice lacking endothelial nitric oxide synthase," *Circulation*, 04(3):342-345, 2001.

Fronk et al., "Noninvasive assessment of endothelial activity in patients with peripheral arterial disease and cardiovascular risk factors," *Endothelium*, 14(4-5):199-205, 2007.

Giugliano et al., "Erectile dysfunction associates with endothelial dysfunction and raise proinflammatory cytokine levels in obese men," *J. Endocrinol. Invest.*, 27(7):665-669, 2004.

Harris et al., "Pegylation: a novel process for modifying pharmacokinetics," *Clin. Pharmacokinet.*, 40:539-551, 2001.

Heil et al., "The 894 G > T variant of endothelial nitric oxide synthase (eNOS) increases the risk of recurrent venous thrombosis through interaction with elevated homocysteine levels", *Journal of Thrombosis and Haemostasis*, 2: 750-753, 2004.

Hingorani et al., "A common variant of the endothelial nitric oxide synthase (Glu298-->Asp) is a major risk factor for coronary artery disease in the UK," *Circulation*, 100(14):1515-1520, 1999.

Iwasaki et al., "Structure and Expression of cDNA for an Inhibitor of Blood Coagulation Isolated from Human Placenta: A New Lipocortin-Like Protein", *J. Biochem.* 102, 1261-1273, 1987.

Kang et al., "Relation of vasodilator response of the brachial artery to inflammatory markers in patients with coronary artery disease," *Echocardiography*, 19(8):661-667, 2002.

Kostner et al., "Inflammation, complement activation and endothelial function in stable and unstable coronary artery disease," *Clin. Chim. Acta*, 365(1-2):129-134, 2006.

Kozlowski et al., "Development of pegylated interferons for the treatment of chronic hepatitis C," *Biodrugs*, 15:419-429, 2001.

Kozlowski et al., "Improvements in protein PEGylation: pegylated interferons for treatment of hepatitis C," *J. Control Release*, 72:217-224, 2001.

Landmesser et al., "Endothelial function: a critical determinant in atherosclerosis?" *Circulation*, 109(Suppl 1):II27-33, 2004.

Lembo et al., "A common variant of endothelial nitric oxide synthase (Glu298Asp) is an independent risk factor for carotid atherosclerosis," *Stroke*, 32(3):735-740, 2001.

Lerman and Zeiher, "Endothelial function: cardiac events," *Circulation*, 111(3):363-368, 2005.

Lowenstein and Tsuda, "N-Ethylmaleimide-sensitive factor: a redox sensor in exocytosis", *Biol Chem.*, 387:1377-1383, 2006.

Ludmer et al., "Paradoxical vasoconstriction induced by acetylocholine in atherosclerotic coronary arteries," *N. Engl. J. Med.*, 315(17):1046-1051, 1986.

Maurer-Fogy et al., "Cloning and expression of cDNA for human vascular anticoagulant, a $Ca^{2+}$-dependent phospholipid-binding protein", *Eur J Biochem.*, 174:585-592, 1988.

Office Communication issued in U.S. Appl. No. 12/808,947, mailed Apr. 12, 2012.

Office Communication issued in U.S. Appl. No. 12/808,947, mailed May 23, 2012.

Office Communication issued in U.S. Appl. No. 12/808,947, mailed Jan. 24, 2013.

Office Communication issued in U.S. Appl. No. 12/808,947, mailed Oct. 15, 2013.

Philip et al., "G894T polymorphism in the endothelial nitric oxide synthase gene is associated with an enhanced vascular responsiveness to phenylephrine," *Circulation*, 99(24):3096-3098, 1999.

Raitakari and Celermajer, "Flow-mediated dilatation," *Br. J. Clin. Pharmacol.*, 50(5):397-404, 2000.

Rand, "Antiphospholipid antibody-mediated disruption of the annexin-V antithrombotic shield: a thrombogenic mechanism for the antiphospholipid syndrome," *J. Autoimmun.*, 15(2):107-11, 2000.

Ravassa et al., "Upregulation of myocardial annexin A5 in hypertensive heart disease: association with systolic dysfunction", *European Heart Journal*, 28:2785-2791, 2007.

Reddy, "Controlled-release, pegylation, liposomal formulations: new mechanisms in the delivery of injectable drugs," *Ann. Pharmacother.*, 34:915-923, 2001.

Roberts et al., "Chemistry for peptide and protein PEGylation," *Adv. Drug Deliv. Rev.*, 54:459-476, 2002.

Rose et al., "Migraine and other headaches: associations with Rose angina and coronary heart disease," *Neurology*, 63(12):2233-2239, 2004.

Shariat-Madar et al., "Bradykinin B2 receptor knockout mice are protected from thrombosis by increase nitric oxide and prostacyclin", *Blood*, 108(1):192-199, 2006.

Shen et al., "Diannexin, a novel annexin V homodimer, protects rat liver transplants against cold ischemia-reperfusion injury," *Am. J. Transplant.*, 7(11):2463-71, 2007.

Silverstro et al., "Inflammatory status and endothelial function in a asymptomatic and symptomatic peripheral arterial disease," *Vasc. Med.*, 8(4):225-232, 2003.

Sorensen et al., "Non-invasive measurement of human endothelium dependent arterial responses: accuracy and reproducibility," *Br. Heart J.*, 74(3):247-253, 1995.

Sugawara et al., Effect of systemic nitric oxide synthase inhibition on arterial stiffness in humans, *Hypertens. Res.*, 30(5):411-415, 2007.

Teoh et al., "Diannexin, a novel annexin V homodimer, provides prolonged protection against hepatic ischemia-reperfusion injury in mice," *Gastroenterology*, 133(2):632-46, 2007.

Ter Avest et al., "What is the role of non-invasive measurements of atherosclerosis in individual cardiovascular risk prediction," *Clin. Sci. (Lond.)*, 112(10):507-506, 2007.

Thiagarajan, P. and C.R. Benedict, "Inhibition of arterial thrombosis by recombinant annexin V in a rabbit carotid artery injury model," *Circulation*, 96(7):2339-47, 1997.

Vermes et al., "A novel assay for apoptosis. Flow cytometric detection of phosphatidylserine expression on early apoptotic cells using fluorescein labelled Annexin V," *J. Immunol. Methods*, 184(1):39-51, 1995.

Veronese, "Peptide and protein PEGylation: a review of problems and solultions," *Biomaterials*, 22:405-417, 2001.

Yang et al., "Arginase activity is increased by thrombin: a mechanism for endothelial dysfunction in arterial thrombosis", *J Am Coll Surg.*, 203:817-826, 2006.

Yetkin et al., "Decreased endothelium-dependent vasodilatation in patients with migraine: a new aspect to vascular pathophysiology of migraine," *Coron. Artery Dis.*, 17(1):29-33,2 006.

Yetkin et al., "Increased dilator response to nitrate and decreased flow-mediated dilatation in migraineurs," *Headache*, 47(1):104-110, 2007.

Yokoyama et al., "HMG-CoA reductase inhibitor protects against in vivo arterial thrombosis by augmenting platelet-derived nitric oxide release in rats", *J Cardiovasc Pharmacol.*, 45(4):375-381, 2005.

COMPOUNDS AND METHODS FOR THE TREATMENT OF VASCULAR DISEASE

CROSS-REFERENCE TO RELATED APPLICATIONS

This application is continuation of U.S. application Ser. No. 14/447,782, filed Jul. 31, 2014, which is a divisional of U.S. application Ser. No. 12/808,947, filed Jun. 17, 2010, which is a national phase application under 35 U.S.C. §371 of International Patent Application No. PCT/GB2008/004195, filed Dec. 18, 2008, which claims priority to U.S. Provisional Patent Application No. 61/014,594, filed Dec. 18, 2007. The entire text of each of the above-referenced disclosures is specifically incorporated herein by reference without disclaimer.

SEQUENCE LISTING

A sequence listing is attached to the present application in a file named EPCLP0017USC1_ST25 (4 KB, created May 4, 2016), and is hereby incorporated by reference herein.

FIELD OF THE INVENTION

The invention relates to novel methods and compositions for the treatment of vascular dysfunction in patients, such as those suffering from conditions including angina pectoris, ischaemic heart disease, peripheral artery disease, systolic hypertension, migraine, type 2 diabetes and erectile dysfunction.

BACKGROUND TO THE INVENTION

The listing or discussion of an apparently prior-published document in this specification should not necessarily be taken as an acknowledgement that the document is part of the state of the art or is common general knowledge.

Angina pectoris ('tight chest') is chest pain due to lack of oxygen in the myocardium. The lack of oxygen is normally due to ischaemia, a reduction in blood supply (and, hence, oxygen supply) to the myocardium. Normally this ischaemia is caused by atherosclerotic plaques in the coronary vessels, but it can also be caused by a local spasm in the coronary vasculature. Other rare causes can be valve disease, severe anemia, aortic stenoses and tachyarrythmias. Angina pectoris is divided into effort angina, angina triggered by physical and/or mental exertion; spasm-angina (variant or Prinzmetal's angina), sudden angina without correlation to a specific situation; and syndrome X, typically an effort related angina but without overt stenosis on angiography. An angina attack normally has a duration of 1 to 5 minutes. If attacks occur at rest, or have a duration exceeding 15 minutes, the disease is referred to as unstable angina and is associated to imminent risk of a cardiovascular event. The condition is classified as unstable angina also when stable angina symptoms are worsened. Unstable angina belongs to the Acute Coronary Syndrome (ACS) and is a critical condition. A myocardial infarction is normally caused by almost complete absence of blood supply to a part of the myocardium, normally caused by the rupture of a coronary atherosclerotic lesion with a subsequent formation of an occluding thrombus.

Peripheral arterial disease (PAD) is a condition with similarities to angina pectoris, but is present in peripheral arteries, normally the lower extremities. Ischaemic pain is common in these patients, and is also normally associated to physical activity. The pain, or cramping sensation, often experienced as a result of physical exercise in PAD patients is normally referred to as intermittent claudication.

Endothelium in Cardiovascular (CV) disease. Vascular dysfunction, in a general sense, characterises most CV disease states, and often involves altered endothelial function. The endothelium is the innermost cell layer in all blood vessels. It is the body's largest endocrine gland, and secretes a number of important factors controlling the circulatory system. Several recent studies have shown that 'endothelial dysfunction' is related to an increased risk for CV events [1]. 'Endothelial dysfunction' is normally measured as a loss of endothelium mediated dilatation, the capacity the endothelium has to dilate blood vessels in response to certain stimuli [2]. There are several ways to measure endothelium mediated dilatation, the most common is dilation of the brachial artery during hyperemia, flow mediated vasodilatation (FMD) [3]. Using such measurements of endothelium mediated dilatation it is shown that vascular function is hampered in individuals suffering from atherosclerosis related diseases (hypertension, hyperlipidemia, diabetes) [4, 5].

The release of Nitric Oxide, NO, from the endothelium is a key event in endothelium mediated dilatation [6]. The key enzyme in the generation of NO is endothelial nitric oxide synthase, eNOS. It has been mostly studied in direct conjunction to the regulation of the vascular system (thrombosis/haemostasis, blood flow regulation and blood vessel growth), but it is also related to the development of atherosclerosis as well as insulin resistance and/or type 2 diabetes (T2DM). For example, mice deficient in eNOS are more prone to become atherosclerotic than mice with normal eNOS function and are also insulin resistant [7].

Normalisation of vascular (dys-)function in an arterial disease state, measured as restoration of normal endothelium mediated dilatation, may or may not be the result of increased release of NO from the endothelium. Vascular dysfunction may, or may not, result from reduced sensitivity of arterial smooth muscles to the NO and/or may, or may not, result from increased metabolism of the NO that is generated. Other mechanisms can also alter vascular function in arterial disease; for example, it is well known that during vascular inflammation the formation of pro-inflammatory and vasoconstrictor substances are increased, and this could offset vasodilatory effects, such as those caused by NO.

Endothelium in angina pectoris and peripheral arterial disease. When acetylcholine is administered into coronary arteries, it triggers the release of NO from the coronary endothelium, which in turn causes dilatation of the coronaries (endothelium mediated dilatation). When this procedure was performed in patients with coronary artery disease, they responded with a 'paradoxical vasoconstriction' [8]. Since then, it has been shown that there is an inappropriate loss of endothelium mediated dilatation in patients suffering from any form of angina pectoris [9, 10], and that this altered function is an important contributor to myocardial ischaemia and, hence, angina pain in these patients.

PAD (normally measured as the reduction in ankle-brachial index (ABI) due to stenosing atherosclerotic lesions) is also characterized by a reduction in endothelium mediated dilatation [11]. In patients where the disease is symptomatic (intermittent claudication) the reduction in endothelium mediated dilatation is greater than in non-symptomatic patients [12].

Systolic hypertension is an important disease in ageing populations, and is normally associated to increased stiffness of the central arterial compartment [13]. It is also shown that NO reduces stiffness [14], and an agent that can restore reduced endothelium mediated dilatation to normal in a patient with systolic hypertension can thus be of therapeutic value.

Another interesting observation is that patients suffering from migraine also have impaired endothelium mediated dilatation, and it was suggested that vascular vasomotion abnormalities can be an important pathophysiological factor in migraine [15, 16]. It is in this context interesting that a mutation in the eNOS gene that is associated to loss of function [17] and is associated to increased risk for CV events [18-20], is also associated to migraine [21].

In yet another aspect of the role of endothelium and NO in disease, erectile dysfunction is also associated with impaired endothelium mediated dilatation [22], and restoring normal endothelium mediated dilatation may also improve erectile dysfunction.

From the above summary, it becomes evident that restoring normal endothelial control of vascular tone by normalising endothelial NO metabolism is a therapeutic opportunity in disease conditions where endothelium mediated dilatation is reduced.

As described above, endothelium mediated dilatation is an important factor in the development of arterial disease. It is also well known that these diseases are also linked to alterations in the haemostatic system, and that vascular inflammation is associated to a state where there is increased risk for arterial thrombus formation.

Annexin A5 is an endogenous protein that binds to charged phospholipids such as phosphatidylserine (PS) [23]. Annexin A5 is a potent anti-thrombotic agent [24], and it is proposed that Annexin A5 by binding to exposed PS can form a 'protective shield' that can inhibit the effects of PS on thrombosis formation [25]. It is interesting in this context that in patients with autoimmune disorders such as APS and/or SLE, there are antibodies in the plasma that can reduce the binding of Annexin A5 to PS on e.g. endothelial cell surfaces, thereby increasing PS exposure. This finding may explain why these patients are at a higher risk for thrombotic events than the general population [23]. Very interestingly, there was a significant reduction in Annexin A5 binding capacity to endothelial cells of serum from controls to SLE patients that had not suffered thrombotic events to SLE patients that had suffered such events [26].

It has been shown that in addition to anti-platelet and anti-coagulant effects of Annexin A5, this protein and an analogue thereof, the Annexin A5 dimer diannexin, is effective in preventing against reperfusion injury in the liver [27], and it improved the outcome of rat liver transplants [28]. Interestingly, in both these studies the treatments were associated with a reduced inflammatory activity in the hepatic endothelium, measured as reduced expression of adhesion molecules. It was suggested that diannexin improved the survival of the liver transplants by an anti-thrombotic effect leading to maintained blood supply to the liver [28].

It has earlier been suggested that Annexin A5 can be used to stabilise atherosclerotic lesions in coronary arteries in patients, which should reduce the risk for myocardial infarction in these patients ([26]; WO 2005/099744).

The bars show mean arterial pressure before (basal) and 3 minutes after the administration of metacholine in untreated and Annexin A5 treated mice, respectively.

Figure 3:
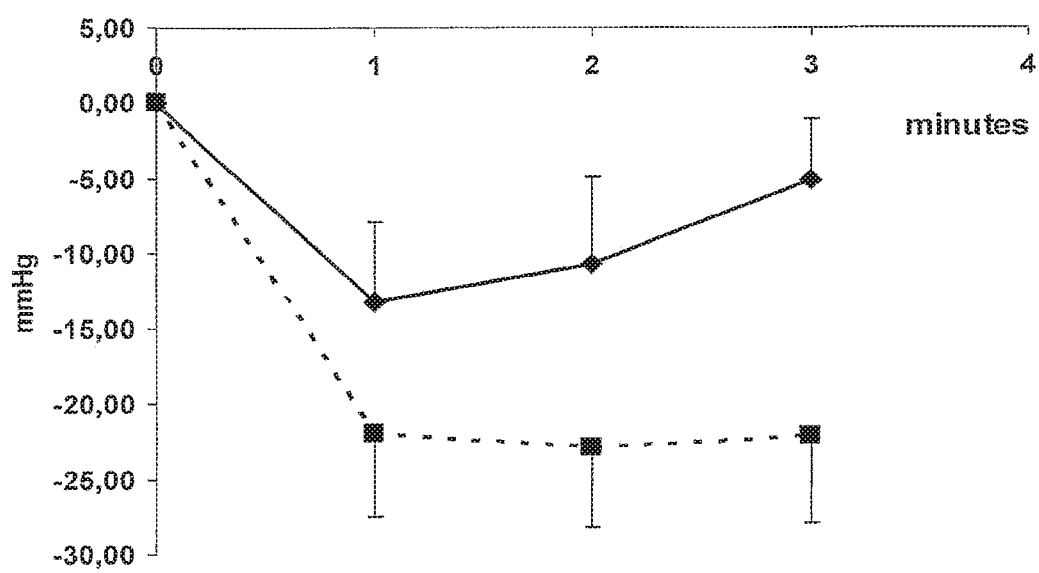
Figure 3:
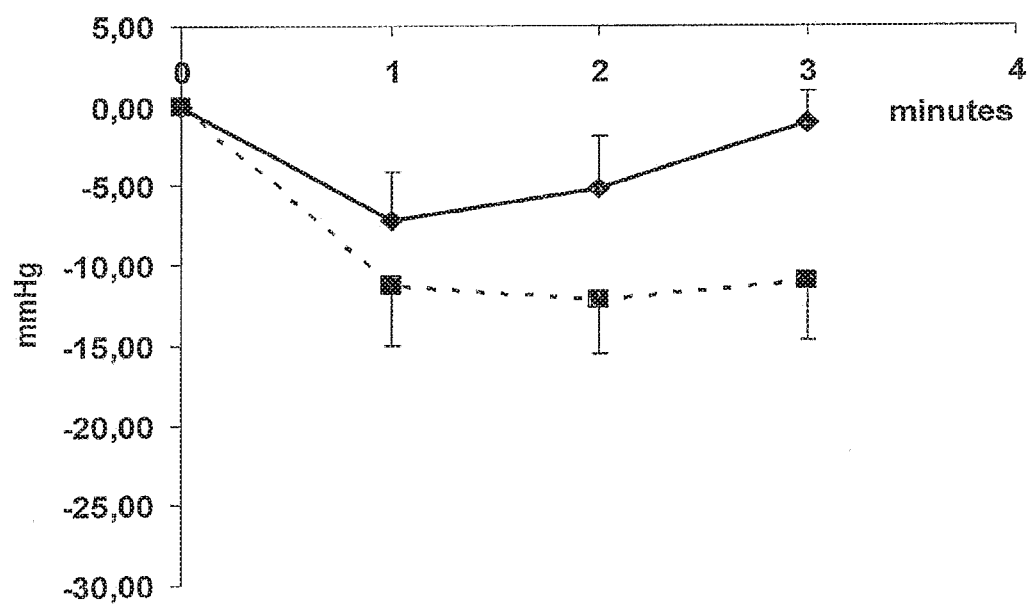

FIG. 3. Summary of the effects of Annexin A5 on metacholine induced changes in systolic and diastolic blood pressure.

Metacholine was injected at time 0 in either control (-♦-) or Annexin A5 treated atherosclerotic mice ( . . . ■ . . . ). Effect on systolic (A) and diastolic (B) blood pressure is shown.

DESCRIPTION OF THE INVENTION

Here we show that Annexin A5 can restore normal endothelium mediated vasodilatation in atherosclerotic mice, by a NO dependent mechanism. Thus, Annexin A5 or analogues thereof provide a new treatment modality with anti-ischaemic effects that can normalise vasomotion abnormalities in diseases where this abnormality is due to a hampered eNOS function or NO bioavailability. There are no previous reports to show that Annexin A5 has anti-ischaemic properties. Such diseases include, but are not limited to, angina pectoris, ischaemic heart disease, peripheral artery disease, systolic hypertension, migraine, type 2 diabetes and erectile dysfunction.

In a first aspect the invention provides a method for the treatment of vascular dysfunction and/or for restoring vascular function comprising administering a therapeutically effective amount of Annexin A5 or a functional analogue or variant thereof to a patient in need of such treatment.

Put another way, the first aspect of the present invention provides Annexin A5 or a functional analogue or variant thereof for use in the treatment of vascular dysfunction and/or for restoring vascular function.

In one embodiment, a patient may be said to suffer from vascular dysfunction if the patient displays a reduced ability to respond to a vasodilating stimulus (optionally, when the mean average response of the patient is assessed over multiple, such as 2, 3, 4, 5, 6, 7, 8, 9 or 10, repetitions of the test) compared to the mean average ability of a control group (10 healthy age-matched, and sex-matched, individuals, optionally wherein each member of the control group is assessed over multiple, such as 2, 3, 4, 5, 6, 7, 8, 9 or 10, repetitions of the test) to respond to the same dosage of the vasodilating stimulus. Suitable vasodilating stimuli that may be used in this assessment include stimuli selected from the group consisting of metacholine, acetylcholine, increased blood flow rate, an NO-generating compound such as nitroglycerine, or a functional test such as an exercise test frequently used in angina patients.

The ability of an individual to respond to a vasodilating stimulus can be assessed by measuring the change in vasodilation caused by the administration of the vasodilating stimulus by intravenous, intra-arterial, sublingual, oral or subcutaneous administration (where the vasodilating stimulus is an agent to be administered to the test subject) or by measuring the response to a functional test, such as an exercise test.

Methods to measure changes in vasodilation are known in the art, and the most appropriate method will be chosen depending on the nature of the vascular dysfunction and/or the type of vasodilating stimulus used.

A common way to measure vasodilation in a test subject, for the purposes of assessing vascular dysfunction, is to measure flow mediated dilatation of the brachial artery following ischaemia induced by a cuff on the upper arm [3]. Previous reports of using this technique have shown that, typically, post-ischaemic hyperemia causes an increase in brachial artery diameter by approximately 10% in the young and healthy individual, whereas in a CVD patient or a type 2 diabetic patient, this response may be e.g. 2-4% or even completely absent. The response can be almost completely inhibited by the administration of an inhibitor of the NO generating enzyme such as 1-NAME.

Alternatively, vasodilation in the resistance arteries of a test subject (e.g. arteries in the lower arm and/or hand) can be measured as changes in blood flow using the art-known technique of plethysmography. In this experimental setting, the vasodilating stimulus could optionally be a local (such as, an intra-arterial) administration of a vasodilating substance, such as acetylcholine.

Coronary vascular function can be assessed by an exercise test such as a bicycle exercise test or a treadmill walk test. In this situation, cardiac ischaemia is measured by changes in the cardiac electrocardiogram (ECG), and/or as the amount of physical work a subject can perform before ischaemic pain (angina) occurs.

Alternatively, large coronary artery function can be evaluated by the local injection of a vasodilating compound during cardiac catheterisation, and the response is evaluated by coronary angiography.

Thus, a patient suffering from vascular dysfunction may display an ability to respond to a vasodilating stimulus that is, at most, 95%, 90%, 85%, 80%, 70%, 60%, 50%, 40%, 30%, 20%, 10% or less than the to the mean average ability of the control group to respond to the same dosage of the vasodilating stimulus.

Patients suffering from diseases such as angina pectoris, ischaemic heart disease, peripheral artery disease, systolic hypertension, migraine, type 2 diabetes and erectile dysfunction commonly display vascular dysfunction.

Thus, vascular dysfunction may be treated and/or vascular function restored by administering a therapeutically effective amount of Annexin A5 or a functional analogue or variant thereof to a patient in need thereof. A therapeutically effective amount of Annexin A5 or a functional analogue or variant thereof, when used in a method according to the present invention to treat vascular dysfunction and/or restore vascular function, can be assessed either by (i) monitoring the response, to a vasodilating stimulus, of a patient suffering from vascular dysfunction, and comparing the observed response before, and then after treatment with Annexin A5 or a functional analogue or variant thereof and/or (ii) monitoring the response, to a vasodilating stimulus, of a patient suffering from vascular dysfunction that has been treated with Annexin A5 or a functional analogue or variant thereof, and comparing the observed response to the mean average ability of the control group of healthy individuals (as defined above, wherein the members of the control group have not been treated with Annexin A5 or a functional analogue or variant thereof) to respond to the same dosage of the vasodilating stimulus; and/or (iii) monitoring the response, to a vasodilating stimulus, of a patient suffering from vascular dysfunction that has been treated with Annexin A5 or a functional analogue or variant thereof, and comparing the observed response to the mean average ability of a control group of condition-matched individuals (10 condition-matched, age-matched, and sex-matched, individuals, optionally wherein each member of the control group is assessed over multiple, such as 2, 3, 4, 5, 6, 7, 8, 9 or 10, repetitions of the test), wherein the members of the control group have not been treated with Annexin A5 or a functional analogue or variant thereof, to respond to the same dosage of the vasodilating stimulus.

The ability of an individual to respond to a vasodilating stimulus can be assessed by measuring the change in vasodilation caused by the administration of the vasodilating stimulus as set out above.

Where the therapeutic effect of the Annexin A5 or a functional analogue or variant thereof is determined as in (i) above, then the level of vasodilating stimulus-induced vasodilatation achieved in the patient prior to treatment with Annexin A5 or a functional analogue or variant thereof may be improved by at least 10%, 20%, 30%, 40%, 50%, 60%, 70%, 80%, 85%, 90%, 95% or at least 100% or even higher values, such as at least 150%, 200%, 250%, 300% or more, by treatment with a therapeutically effective amount of Annexin A5 or a functional analogue or variant thereof in accordance with the present invention, compared to the pre-treatment level of vasodilating stimulus-induced vasodilatation achieved in the patient.

Where the therapeutic effect of the Annexin A5 or a functional analogue or variant thereof is determined as in (ii) above, then the level of vasodilating stimulus-induced vasodilatation achieved in the patient following treatment with Annexin A5 or a functional analogue or variant thereof may be improved to a level that is at least 10%, 20%, 30%, 40%, 50%, 60%, 70%, 80%, 85% 90%, 95%, 98%, 99%, substantially about 100% or more compared to the mean average level of vasodilating stimulus-induced vasodilation observed in the control group.

Where the therapeutic effect of the Annexin A5 or a functional analogue or variant thereof is determined as in (iii) above, then the level of vasodilating stimulus-induced vasodilatation achieved in the patient following treatment with Annexin A5 or a functional analogue or variant thereof may be improved to a level that is at greater than 100%, such as at least 150%, 200%, 250%, 300%, or more, compared to the mean average level of vasodilating stimulus-induced vasodilation observed in the control group.

The vascular dysfunction may be associated with impaired endothelium mediated vasodilatation and/or may be associated with a reduced eNOS activity and/or a reduced NO bioavailability.

The present invention also provides, as a second aspect, a method for reducing ischemic pain, such as angina pectoris or pain associated with peripheral arterial disease (PAD), by administering a therapeutically effective amount of Annexin A5 or a functional analogue or variant thereof to a patient in need of such treatment.

Put another way, the second aspect of the present invention provides Annexin A5 or a functional analogue or variant thereof for use in reducing ischemic pain.

The patient treated by the first or second aspect of the invention may, or may not, be a subject suffering from a disease selected from angina pectoris, ischaemic heart disease, peripheral artery disease, systolic hypertension, migraine, type 2 diabetes and erectile dysfunction, and thus the vascular dysfunction and/or ischemic pain may be associated with any one or more of these diseases.

Where the patient is suffering from angina pectoris, it may, or may not, be caused by any one of atherosclerotic plaques in the coronary vessels, local spasm in the coronary vasculature, valve disease, severe anaemia, aortic stenoses, and/or tachyarrythmias. The patient may, or may not, be suffering from effort angina, spasm-angina (variant or Prinzmetal's angina), sudden angina, or syndrome X. The patient may, or may not, be suffering from stable, or unstable, angina.

Treatment of vascular dysfunction and/or restoring vascular function in patients with conditions such as angina pectoris in accordance with the present invention may also reduce the risk of the onset of acute myocardial infarction (AMI) and its following complications such as those listed by the international classification of disease (ICD) at the world-wide-web who.int/classifications/apps/icd/icd10online/, under category 1.23 which includes haemopericardium following AMI (I23.0), atrial septal following AMI (I23.1), ventricular septal defect following AMI (I23.2), rupture of cardiac wall without haemopericardium following AMI (I23.3), rupture of chordae tendineae following AMI (I23.4), rupture of papillary muscle following AMI (I23.5), thrombosis of atrium, auricular appendage, and ventricle following AMI (I23.6) and other current complications following AMI (I23.8).

Where the patient is suffering from ischemic heart disease, the patient may, or may not, suffer from atherosclerosis, or angina without overt atherosclerosis.

The patient may, or may not, be a human. The patient may, or may not be a non-human animal, such as a domestic animal (for example, cat, dog, rabbit, cow, sheep, pig, mouse or other rodent).

In a third aspect, the invention provides a method for the treatment, prevention, or reduction of risk of onset of a vascular disease comprising administering a therapeutically effective amount of Annexin A5 or a functional analogue or variant thereof to a patient in need of such treatment.

Put another way, the third aspect of the present invention provides Annexin A5 or a functional analogue or variant thereof for use in the treatment, prevention, or reduction of risk of onset of a vascular disease.

The vascular disease treated by the third aspect of the invention can be associated with impaired endothelium mediated vasodilatation, reduced eNOS activity and/or reduced NO bioavailability. The vascular disease treated by the third aspect of the invention may, or may not, be a disease selected from angina pectoris, ischaemic heart disease, peripheral artery disease, systolic hypertension, migraine, type 2 diabetes and erectile dysfunction, such as those conditions discussed above in more detail in respect of the first and second aspects of the invention.

Treatment of conditions such as angina pectoris in accordance with the present invention may also reduce the risk of the onset of acute myocardial infarction (AMI) and its following complications such as those listed by the international classification of disease (ICD) at the world-wide-web who.int/classifications/apps/icd/icd10online/, under category 1.23 which includes haemopericardium following AMI (I23.0), atrial septal following AMI (I23.1), ventricular septal defect following AMI (I23.2), rupture of cardiac wall without haemopericardium following AMI (I23.3), rupture of chordae tendineae following AMI (I23.4), rupture of papillary muscle following AMI (I23.5), thrombosis of atrium, auricular appendage, and ventricle following AMI (I23.6) and other current complications following AMI (I23.8).

Thus, the third aspect of the present invention includes a method for reducing the risk of onset of AMI or its following complications by the treatment of a vascular disease comprising administering a therapeutically effective amount of Annexin A5 or a functional analogue or variant thereof to a patient.

The AnnexinA5 or the functional analogue or variant thereof can be administered in conjunction with (that is, separately, simultaneously, or sequentially with) one or more further active agent(s), such as
- a thrombolytic therapeutic, such as tissue plasminogen activator, urokinase, or a bacterial enzyme,
- an antiplatelet agent, such as aspirin or clopidogrel (Plavix), and/or
- nitroglycerin and/or morphine.

In a fourth aspect, the invention provides a pharmaceutical composition comprising a therapeutically effective amount of Annexin A5 or a functional analogue or variant thereof for the treatment of a vascular disease selected from angina pectoris, ischaemic heart disease, peripheral artery disease, systolic hypertension, migraine, and erectile dysfunction, as discussed above in respect of the first and second aspect of the invention. The vascular disease can be associated with (in other words, a patient with the vascular disease may display) impaired endothelium mediated vasodilatation, a reduced eNOS activity and/or a reduced NO bioavailability.

In a fifth aspect, the invention provides a pharmaceutical composition comprising a therapeutically effective amount of Annexin A5 or a functional analogue or variant thereof for the treatment of a vascular dysfunction and/or restoring vascular function. The vascular dysfunction can be associated with (in other words, a patient with the vascular dysfunction may display) impaired endothelium mediated vasodilatation, a reduced eNOS activity, and/or a reduced NO bioavailability. The vascular dysfunction can be associated with a disease selected from angina pectoris, ischaemic heart disease, peripheral artery disease, systolic hypertension, migraine, type 2 diabetes and erectile dysfunction, as discussed above in respect of the first and second aspect of the invention.

A pharmaceutical composition according to the fourth or fifth aspects of the invention may thus comprise Annexin A5 or a functional analogue or variant thereof in admixture with a pharmaceutically or veterinarily acceptable adjuvant, diluent or carrier, which will typically be selected with regard to the intended route of administration and standard pharmaceutical practice. The composition may be in the form of immediate-, delayed- or controlled-release applications. Preferably, the formulation is a unit dosage containing a daily dose or unit, daily sub-dose or an appropriate fraction thereof, of the active ingredient.

The pharmaceutical composition according to the invention may, or may not, be intended for, and, thus formulated in a manner suitable for, parenteral, intravenous, intra-arterial, intraperitoneal, intra-muscular or subcutaneous administration, or they may be administered by infusion techniques. They may be best used in the form of a sterile aqueous solution which may contain other substances, for example, enough salts or glucose to make the solution isotonic with blood. The aqueous solutions may be suitably buffered (preferably to a pH of from 3 to 9), if necessary. The preparation of suitable pharmaceutical formulations under sterile conditions is readily accomplished by standard pharmaceutical techniques well-known to those skilled in the art.

Such formulations may include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

A therapeutically effective amount of Annexin A5 or a functional analogue or variant thereof for administration to a patient, such as a human patient, on the basis of a daily dosage level may be from 0.01 to 1000 mg of Annexin A5 or a functional analogue or variant thereof per adult (for example, from about 0.001 to 20 mg per kg of the patient's body weight, such as 0.01 to 10 mg/kg, for example greater than 0.1 mg/kg and less than 20, 10, 5, 4, 3 or 2 mg/kg, such as about 1 mg/kg), administered in single or divided doses.

The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

For veterinary use, a compound of the invention is administered as a suitably acceptable formulation in accordance with normal veterinary practice and the veterinary surgeon will determine the dosing regimen and route of administration which will be most appropriate for a particular animal.

In a sixth aspect, the invention provides use of Annexin A5 or a functional analogue or variant thereof in the manufacture of a medicinal product for the treatment, prevention or reduction of risk of onset of a condition defined above in the context of any one of the first, second or third aspects of the present invention.

The Annexin A5 or the functional analogue or variant thereof according to the invention can be human Annexin A5 (SEQ ID NO:1), an allelic or genetic variant thereof, a mammalian orthologue thereof, or an allelic or genetic variant thereof. Preferably the functional analogue or variant of Annexin A5 according to the invention is more than 50%, 60%, 70%, 75%, such as more than 80% or 85%, more than 90%, or preferably more than 95% or 99% identical to human Annexin A5, SEQ ID NO:1.

The percent identity between two amino acid sequences is determined as follows. First, an amino acid sequence is compared to, for example, SEQ ID NO:1 using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information web site at ncbi.nlm.nih.gov. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq—i c:\seq1.txt-j c:\seq2.txt-p blastp-o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences.

The percent identity is determined by dividing the number of matches by the length of the sequence set forth in an identified sequence followed by multiplying the resulting value by 100. For example, if a sequence is compared to the sequence set forth in SEQ ID NO:1 (the length of the sequence set forth in SEQ ID NO:1 is 320) and the number of matches is 288, then the sequence has a percent identity of 90 (i.e., 288÷320*100=90) to the sequence set forth in SEQ ID NO:1.

Thus, a functional analogue or variant of Annexin A5 may be a protein wherein at one or more positions there have been amino acid insertions, deletions, or substitutions, either conservative or non-conservative, provided that such changes result in a protein whose basic properties to function in an equivalent manner to Annexin A5 have not significantly been changed. "Significantly" in this context means that one skilled in the art would say that the properties of the variant may still be different but would not be unobvious over the ones of the original protein.

By "conservative substitutions" is intended combinations such as Gly, Ala; Val, Ile, Leu; Asp, Glu; Asn, Gln; Ser, Thr; Lys, Arg; and Phe, Tyr.

Such variants may be made using the methods of protein engineering and site-directed mutagenesis which are well known in the art.

The functional analogue or variant of Annexin A5 according to the invention may, or may not, be a dimer of Annexin A5 or a functional analogue or variant thereof, or may or may not, be a PEGylated Annexin A5 or a functional analogue or variant thereof. DiAnnexinA5 and PEGylated AnnexinA5 are disclosed in WO 02/067857.

PEGylation is a method well known to those skilled in the art wherein a polypeptide or peptidomimetic compound (for the purposes of the present invention, Annexin A5 or the functional analogue or variant) is modified such that one or more polyethylene glycol (PEG) molecules are covalently attached to the side chain of one or more amino acids or derivatives thereof. It is one of the most important molecule altering structural chemistry techniques (MASC). Other MASC techniques may be used; such techniques may improve the pharmacodynamic properties of the molecule, for example extending its half life in vivo. A PEG-protein conjugate is formed by first activating the PEG moiety so that it will react with, and couple to, the protein or peptidomimetic compound of the invention. PEG moieties vary considerably in molecular weight and conformation, with the early moieties (monofunctional PEGs; mPEGs) being linear with molecular weights of 12 kDa or less, and later moieties being of increased molecular weights. PEG2, a recent innovation in PEG technology, involves the coupling of a 30 kDa (or less) mPEG to a lysine amino acid (although PEGylation can be extended to the addition of PEG to other amino acids) that is further reacted to form a branched structure that behaves like a linear mPEG of much greater molecular weight (Kozlowski et al., (2001), Biodrugs 15, 419-429). Methods that may be used to covalently attach the PEG molecules to polypeptides are further described in Roberts et al., (2002) Adv Drug Deliv Rev, 54, 459-476, Bhadra et al., (2002) Pharmazie 57, 5-29, Kozlowski et al., (2001) J Control Release 72, 217-224, and Veronese (2001) Biomaterials 22, 405-417 and references referred to therein.

The advantages of PEGylation to the polypeptide or peptidomimetic compound of the invention include reduced renal clearance which, for some products, results in a more sustained adsorption after administration as well as restricted distribution, possibly leading to a more constant and sustained plasma concentrations and hence an increase in clinical effectiveness (Harris et al., (2001) Clin Pharmacokinet 40, 539-551). Further advantages can include reduced immunogenicity of the therapeutic compound (Reddy, (2001) Ann Pharmacother 34, 915-923), and lower toxicity (Kozlowski et al., (2001), Biodrugs 15, 419-429).

The functional analogue or variant of Annexin A5 according to the invention can be a fusion protein comprising the sequence of Annexin A5 or a variant thereof. Thus, for example, Annexin A5 or a variant thereof can be fused to one or more fusion partner polypeptide sequence(s) so as to extend the half-life of the molecule within a patient's circulatory system and/or add further functionality to the molecule.

By a "functional" analogue or variant of Annexin A5 is meant a protein capable of binding to phosphatidylserine on a biological membrane, preferably to a level that is at least 10%, 20%, 30%, 40%, 50%, 60%, 70%, 80%, 90%, 95%, 99% or about 100% of that displayed by human Annexin A5 (SEQ ID NO:1) under the same conditions. A suitable method for measuring Annexin A5 binding to phosphatidylserine on a biological membrane is known in the art [29].

A "functional" analogue or variant of Annexin A5 may, additionally, or alternatively, also possess at least 10%, 20%, 30%, 40%, 50%, 60%, 70%, 80%, 90%, 95%, 99% or about 100% of the therapeutic activity human Annexin A5 (SEQ ID NO:1) when used at the same (i.e. molar equivalent) dosage, for treatment of vascular dysfunction, for restoring vascular function, for reducing ischemic pain and/or for the treatment of a vascular disease in accordance with any of the first, second or third aspects of the invention.

In this context, the therapeutic activity of a "functional" analogue or variant of Annexin A5 may be determined, compared to that of human Annexin A5 (SEQ ID NO:1), by comparing the ability of a molar equivalent amount of the functional analogue or variant and of human Annexin A5 to treat vascular dysfunction as described above, and/or to restore the ability of apoE$^{(-/-)}$ mice kept on a diet of high lipid and cholesterol for 4 months to display endothelium mediated dilation in response to intraperitoneal administration of 3 µg/kg bw (10 µl/g) metacholine (Sigma), when the mice are administered, by intraperitoneal injection, molar equivalent amount of either Annexin A5 or the analogue or variant in question once a day in the morning for 3 consecutive days, the final injection being approximately 2-3 hours before the administration of metacholine, and wherein the extent of endothelium mediated dilation in the test subjects is measured by assessing blood pressure via catheterisation of the left carotid artery, such as using the methodology set out in the following example.

"Vascular disease associated with a reduced eNOS activity or a reduced NO bioavailability" as used herein refers to a vascular disease which is caused by, causes or leads to, has a common cause with, or is co-existing with a reduced eNOS activity or a reduced NO bioavailability.

"Vascular dysfunction associated with a disease" as used herein refers to a vascular dysfunction, such as a loss of endothelium mediated vasodilatation, which is caused by, causes or leads to, has a common cause with, or is co-existing with the disease in question. Examples of such diseases are provided above.

EXAMPLE

Mice that are made deficient in apolipoprotein E by gene targeting (apoE$^{(-/-)}$ mice) are hyperlipidemic and develop atherosclerosis. This process is accelerated by feeding the mice a so called Western diet, e.g. Harlan Teklad TD.88137. This is a purified diet with 21% anhydrous milkfat (butterfat), 34% sucrose, and a total of 0.2% cholesterol which, compared to normal mouse diets, contains extra lipids and some cholesterol. We gave a such diet to male apoE$^{(-/-)}$ mice for at least 4 months, after which we evaluated the effects of Annexin A5 on endothelium mediated dilatation. In this way, the mice will develop vascular disease including an impairment of endothelium mediated dilatation that is typical for patients with e.g. angina pectoris, hypertension, diabetes and hyperlipidemia.

Evaluation of Endothelium Mediated Dilatation in Anaesthetized Mice.

Anaesthesia was induced by 4.5% Isofluran (Isoba®vet, Schering-Plough Animal Health, Denmark) and then maintained by supplying Isofluran as needed (normally 1.5-2%).

For blood pressure measurements we performed a catheterisation (Samba Sensor preclin 420 LP, Västra Frö lunda, Sweden) of the left carotid artery. Thereafter the catheter was gently moved into aortic arch. The Samba sensor was connected to a Samba 3200 unit, from which the data was transferred to and stored in the Powerlab software (AD Instrument, version 5) at 2 kHz.

Mice were then allowed to stabilise for approx. 15 minutes. Endothelium mediated dilatation was then induced by the intraperitoneal (ip) administration of 3 µg/kg bw (10 µl/g) metacholine (Sigma), and blood pressure was measured for 5 minutes. When endothelium mediated dilatation is stimulated systemically, total peripheral vascular resistance is reduced, and the vasodilatation can be measured as a reduction in arterial blood pressure. Metacholine causes a transient stimulation of the arterial endothelium to release NO, which in turn will cause endothelium mediated vasodilatation in a normal, healthy mouse. After the effect of metacholine has disappeared and baseline pressure is again established, an ip dose of 50 mg/kg bw L-NAME (N$^G$-nitro-L-arginine methyl ester) (Sigma) was given. This is an inhibitor of the enzyme eNOS, which converts arginine to NO (and citrulline), and thus responsible for the endothelium mediated dilatation. Blood pressure was then followed until a new plateau was reached (12-15 minutes), after which metacholine 3 µg/kg was again administered and blood pressure measured for 5 minutes.

Results.

Figure 1:
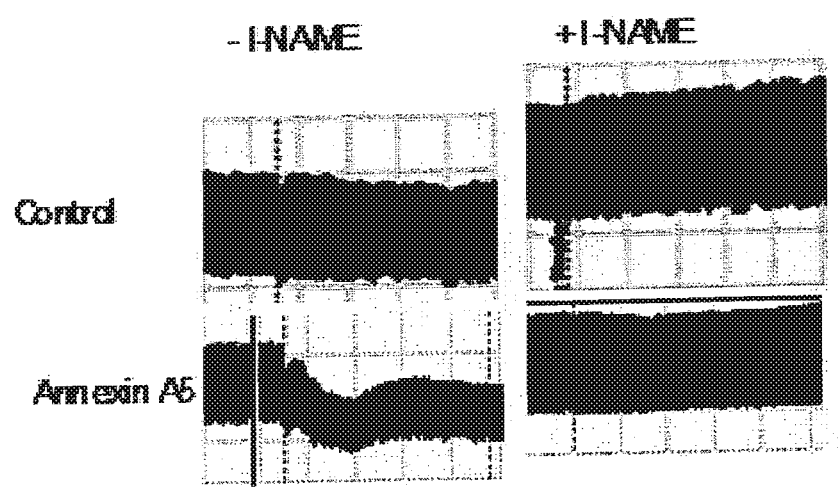
FIG. 1. Annexin A5 restore endothelium mediated vasodilatation Representative recordings of blood pressure in a control apoE$^{(-/-)}$ mouse (upper trace) and an Annexin A5 treated mouse (lower trace). Metacholine was injected as indicated by the dotted line. Panels to the right with previous administration of the inhibitor of eNOS, 1-NAME.

Normal mice will respond to metacholine injections by a reduction in both systolic and diastolic blood pressure. After 4 months on the western diet, a pilot study of some apoE$^{(-/-)}$ mice was performed to verify that the normal response to a metacholine injection was absent. When this had been established, mice received 1 mg recombinant human Annexin A5 (Bender Medsystems, Vienna, Austria)/kg bw or its vehicle (saline) in the morning for 3 days by intraperitoneal injection. On the 3$^{rd}$ day, and approximately 2-3 hours after the final injection of Annexin A5/vehicle, endothelium mediated dilatation was investigated as described above. FIG. 1 is an example of a typical experiment:

FIG. 1 shows representative recordings of blood pressure in a control apoE$^{(-/-)}$ mouse (upper trace) and an Annexin A5 treated mouse (lower trace). Metacholine was injected as indicated by the dotted line. The mouse treated with Annexin A5 responded with a profound vasodilatation, a marked improvement compared to the control mouse, that hardly responded at all (left panels). The panel to the right shows that this response was inhibited by previous administration of the inhibitor of eNOS, 1-NAME, verifying that the effect of Annexin A5 on endothelium mediated dilatation was mediated by NO. The reduction in systolic blood pressure was larger than the reduction in diastolic blood pressure.

Figure 2:
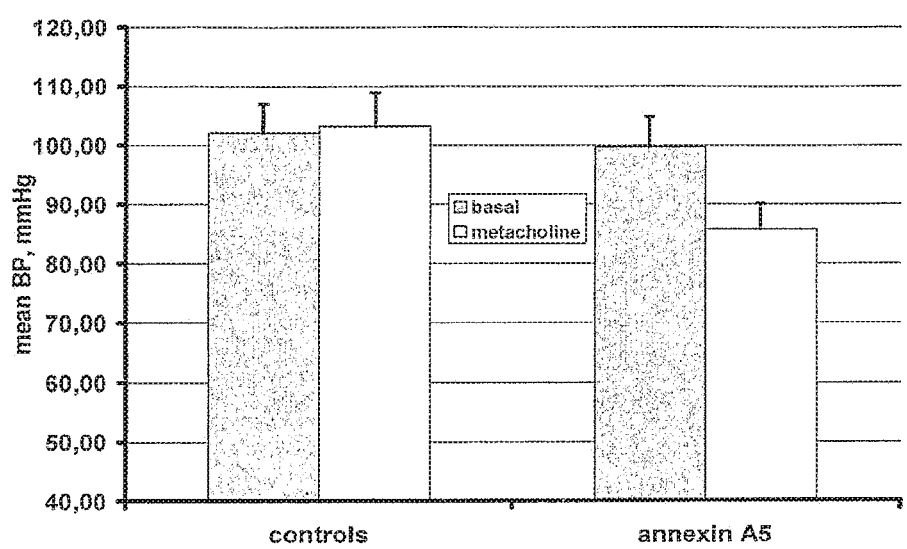
FIG. 2. Summary of the effects of Annexin A5 on endothelium mediated vasodilatation measured as blood pressure.

FIG. 2 summarises the effects of Annexin A5 on endothelium mediated dilatation in this model of angina pectoris and shows that in the untreated apoE$^{(-/-)}$ mice injection of metacholine did not reduce mean blood pressure. In contrast, Annexin A5 treated apoE$^{(-/-)}$ mice responded to metacholine with a significant reduction in blood pressure. As this effect was blocked by 1-NAME we concluded that the effect was mediated by eNOS/nitric oxide.

FIG. 3 shows that Annexin A5 treatment for 3 days significantly improved the endothelium mediated reduction in both systolic (A) and diastolic (B) blood pressures. Treatment with Annexin A5 restored not only the function of resistance arteries as indicated by the reduction in diastolic blood pressure, but as the effect on systolic blood pressure was larger than effects on diastolic blood pressure, the drug treatment also increased compliance of the central arteries.

This study shows for the first time that Annexin A5 can restore normal function of the endothelium in a mouse model of artery disease/angina pectoris. The effect was mediated by restoration of the NO metabolism in the endothelium. The findings show the potential of Annexin A5 to exert anti-ischaemic effects. The most common treatment of angina pectoris is restore blood flow to ischaemic myocardial tissue by the administration of exogenous NO, normally in the form of organic nitrates such as nitroglycerin. As repeated use of exogenous organic nitrates is associated to development of nitrate tolerance, this treatment is normally limited to acute ischaemic situations. Here we have shown the potential of Annexin A5 as an alternative anti-ischaemic treatment in vascular diseases in which normal NO metabolism is hampered.

Summary. Arterial vasomotion abnormalities due to impaired endothelium mediated dilatation is common in most patients with ischaemic vascular disease. In a model of such disease, it was surprisingly found that Annexin A5 restored the impaired endothelium mediated function through a NO dependent mechanism.

REFERENCES

1. Lerman, A. and A. M. Zeiher, *Endothelial function: cardiac events*. Circulation, 2005. 111(3): p. 363-8.
2. Landmesser, U., B. Hornig, and H. Drexler, *Endothelial function: a critical determinant in atherosclerosis?* Circulation, 2004. 109(21 Suppl 1): p. 1127-33.
3. Sorensen, K. E., et al., *Non-invasive measurement of human endothelium dependent arterial responses: accuracy and reproducibility*. Br Heart J, 1995. 74(3): p. 247-53.
4. Raitakari, O. T. and D. S. Celermajer, *Flow-mediated dilatation*. Br J Clin Pharmacol, 2000. 50(5): p. 397-404.
5. Ter Avest, E., A. F. Stalenhoef, and J. de Graaf, *What is the role of non-invasive measurements of atherosclerosis in individual cardiovascular risk prediction?* Clin Sci (Lond), 2007. 112(10): p. 507-16.
6. Doshi, S. N., et al., *Flow-mediated dilatation following wrist and upper arm occlusion in humans: the contribution of nitric oxide*. Clin Sci (Lond), 2001. 101(6): p. 629-35.
7. Duplain, H., et al., *Insulin resistance, hyperlipidemia, and hypertension in mice lacking endothelial nitric oxide synthase*. Circulation, 2001. 104(3): p. 342-5.
8. Ludmer, P. L., et al., *Paradoxical vasoconstriction induced by acetylcholine in atherosclerotic coronary arteries*. N Engl J Med, 1986. 315(17): p. 1046-51.
9. Kang, S. M., et al., *Relation of vasodilator response of the brachial artery to inflammatory markers in patients with coronary artery disease*. Echocardiography, 2002. 19(8): p. 661-7.
10. Kostner, K. M., et al., *Inflammation, complement activation and endothelial function in stable and unstable coronary artery disease*. Clin Chim Acta, 2006. 365(1-2): p. 129-34.
11. Fronek, A., D. G. DiTomasso, and M. Allison, *Noninvasive assessment of endothelial activity in patients with peripheral arterial disease and cardiovascular risk factors*. Endothelium, 2007. 14(4-5): p. 199-205.
12. Silvestro, A., et al., *Inflammatory status and endothelial function in asymptomatic and symptomatic peripheral arterial disease*. Vasc Med, 2003. 8(4): p. 225-32.
13. Chobanian, A. V., *Clinical practice. Isolated systolic hypertension in the elderly*. N Engl J Med, 2007. 357(8): p. 789-96.
14. Sugawara, J., et al., *Effect of systemic nitric oxide synthase inhibition on arterial stiffness in humans*. Hypertens Res, 2007. 30(5): p. 411-5.
15. Yetkin, E., et al., *Decreased endothelium-dependent vasodilatation in patients with migraine: a new aspect to vascular pathophysiology of migraine*. Coron Artery Dis, 2006. 17(1): p. 29-33.
16. Yetkin, E., et al., *Increased dilator response to nitrate and decreased flow-mediated dilatation in migraineurs*. Headache, 2007. 47(1): p. 104-10.
17. Philip, I., et al., *G894T polymorphism in the endothelial nitric oxide synthase gene is associated with an enhanced vascular responsiveness to phenylephrine*. Circulation, 1999. 99(24): p. 3096-8.
18. Hingorani, A. D., et al., *A common variant of the endothelial nitric oxide synthase (Glu298→Asp) is a major risk factor for coronary artery disease in the UK*. Circulation, 1999. 100(14): p. 1515-20.
19. Lembo, G., et al., *A common variant of endothelial nitric oxide synthase (Glu298Asp) is an independent risk factor for carotid atherosclerosis*. Stroke, 2001. 32(3): p. 735-40.
20. Rose, K. M., et al., *Migraine and other headaches: associations with Rose angina and coronary heart disease*. Neurology, 2004. 63(12): p. 2233-9.
21. Borroni, B., et al., *Endothelial nitric oxide synthase (Glu298Asp) polymorphism is an independent risk factor for migraine with aura*. Headache, 2006. 46(10): p. 1575-9.
22. Giugliano, F., et al., *Erectile dysfunction associates with endothelial dysfunction and raised proinflammatory cytokine levels in obese men*. J Endocrinol Invest, 2004. 27(7): p. 665-9.
23. Cederholm, A. and J. Frostegard, *Annexin A5 as a novel player in prevention of atherothrombosis in SLE and in the general population*. Ann N Y Acad Sci, 2007. 1108: p. 96-103.

24. Thiagarajan, P. and C. R. Benedict, *Inhibition of arterial thrombosis by recombinant annexin V in a rabbit carotid artery injury model.* Circulation, 1997. 96(7): p. 2339-47.

25. Rand, J. H., *Antiphospholipid antibody-mediated disruption of the annexin-V antithrombotic shield: a thrombogenic mechanism for the antiphospholipid syndrome.* J Autoimmun, 2000. 15(2): p. 107-11.

26. Cederholm, A., et al., *Decreased binding of annexin v to endothelial cells: a potential mechanism in atherothrombosis of patients with systemic lupus erythematosus.* Arterioscler Thromb Vasc Biol, 2005. 25(1): p. 198-203.

27. Teoh, N. C., et al., *Diannexin, a novel annexin V homodimer, provides prolonged protection against hepatic ischemia-reperfusion injury in mice.* Gastroenterology, 2007. 133(2): p. 632-46.

28. Shen, X. D., et al., *Diannexin, a novel annexin V homodimer, protects rat liver transplants against cold ischemia-reperfusion injury.* Am J Transplant, 2007. 7(11): p. 2463-71.

29. Vermes, I., et al., *A novel assay for apoptosis. Flow cytometric detection of phosphatidylserine expression on early apoptotic cells using fluorescein labelled Annexin V.* J Immunol Methods, 1995. 184(1): p. 39-51.

The invention claimed is:

1. A method for the treatment of peripheral artery disease comprising administering a therapeutically effective amount of recombinant human Annexin A5 to a patient in need of such treatment.

2. The method according to claim 1, wherein the therapeutically effective amount of recombinant human Annexin A5 is administered parenterally, intravenously, intra-arterially, intra-peritoneally, intra-muscularly or subcutaneously.

3. The method according to claim 1, wherein the recombinant human Annexin A5 is produced by expressing a gene that encodes a protein consisting of the sequence of SEQ ID NO: 1.

* * * * *

SEQUENCE LISTING

<160> NUMBER OF SEQ ID NOS: 1

<210> SEQ ID NO 1
<211> LENGTH: 320
<212> TYPE: PRT
<213> ORGANISM: Homo sapiens

<400> SEQUENCE: 1

```
Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
            20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
    50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285
```

-continued

```
Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320
```